United States Patent [19]
Burgreen et al.

[11] Patent Number: 6,093,001
[45] Date of Patent: Jul. 25, 2000

[54] ROTARY PUMP HAVING A BEARING WHICH DISSIPATES HEAT

[75] Inventors: Gregory W. Burgreen, Pittsburgh; James F. Antaki, Allison Park, both of Pa.

[73] Assignee: University of Pittsburgh, Pittsburgh, Pa.

[21] Appl. No.: 08/848,980

[22] Filed: May 2, 1997

[51] Int. Cl.[7] .................................................... F04B 17/00
[52] U.S. Cl. ................... 417/423.8; 417/423.12; 417/356; 415/176; 415/178; 415/900
[58] Field of Search ............................ 417/423.8, 423.12, 417/356, 350; 415/176, 178, 900

[56] References Cited

U.S. PATENT DOCUMENTS

| | | | |
|---|---|---|---|
| 4,704,121 | 11/1987 | Moise | 415/112 |
| 4,922,822 | 5/1990 | Bierschenk et al. | |
| 4,994,078 | 2/1991 | Jarvik . | |
| 5,275,580 | 1/1994 | Yamazaki . | |
| 5,322,413 | 6/1994 | Vescovini et al. | 415/900 |
| 5,360,317 | 11/1994 | Clausen et al. | 415/900 |
| 5,399,074 | 3/1995 | Nosé et al. | 417/423.1 |
| 5,527,159 | 6/1996 | Bozeman, Jr. et al. | |
| 5,575,630 | 11/1996 | Nakazawa et al. | |
| 5,588,812 | 12/1996 | Taylor et al. | |
| 5,618,167 | 4/1997 | Hirakawa et al. | 417/423.8 |
| 5,700,134 | 12/1997 | Huntley | 417/153 |
| 5,707,218 | 1/1998 | Maher et al. | 417/356 |
| 5,746,575 | 5/1998 | Westphal et al. | 415/900 |

FOREIGN PATENT DOCUMENTS

| | | |
|---|---|---|
| 0 759 507 A1 | 2/1997 | European Pat. Off. . |
| WO 85/01436 | 4/1985 | WIPO . |

*Primary Examiner*—Timothy S. Thorpe
*Assistant Examiner*—Cheryl J. Tyler
*Attorney, Agent, or Firm*—Woodcock Washburn Kurtz Mackiewicz & Norris LLP

[57] ABSTRACT

A rotary pump having a housing defining a flow path, a stator attached to the housing, a rotor which contacts the stator and rotates thereabout, a motor for rotating the rotor and semiconductor-based electronic components which draws the heat created by the frictional contact between the stator and rotor away from blood flowing through the housing. The rotary pump can be a centrifugal pump having a housing with a base plate, a rotor with rotor blades and a stator wherein the base plate and the rotor are shaped and proportioned such that blood is prevented from stagnating/collecting between the rotor blades and base plate.

21 Claims, 7 Drawing Sheets

ROTARY PUMP HAVING A BEARING WHICH DISSIPATES HEAT

BACKGROUND OF THE INVENTION

1. Field of the Invention

This invention relates to a rotary blood pump having a housing, a stator and a rotor wherein the rotor is rotatably connected to the stator. More particularly, this invention concerns a rotary pump having a rotor rotatably connected to the stator and which incorporates a semiconductor-based electronic component to draw heat created by the frictional contact between the rotor and the stator away from the rotor thus, preventing coagulation and destruction of blood flowing through the rotary pump.

2. Description of the Related Art

One type of conventional axial flow rotary pump 10, shown in FIG. 1, comprises a pump housing 12 which defines a blood flow path 14 and which houses a rotor 16 and stator members 18. The rotor 16 is substantially cylindrical with a tail 20 and a nose 22 and has impeller blades 24 extending from the rotor 16. A contact-type bearing 25 is positioned at the nose 22 and another contact-type bearing 27 is positioned at the tail 20. Contact-type bearings may be (a) roller-type, (b) journal-type, or (c) pivot-type. The journal-type comprises bearings implementing a hydrodynamic film, typically annular for radial loads, or disk-like for thrust loads. This type of bearing is illustrated in U.S. Pat. No. 4,994,078 issued to Jarvik and U.S. Pat. No. 5,275,580 issued to Yamazaki et al. The pivot-type comprises bearings using either point contact (like jewel bearings used in clock mechanisms) or a ball-and-cup connection. This type of bearing is illustrated in U.S. Pat. No. 5,588,812 issued to Taylor et al., U.S. Pat. No. 5,527,159 issued to Bozeman Jr., et al. and U.S. Pat. No. 5,575,630 issued to Nakazawa et al. For the purposes of this discussion, a pivot-type ball-and-cup bearing will be assumed, although any of the aforementioned contact-type bearings are applicable.

The stator member 18 located at the inlet 30 has stator inlet blades 32 and a cup 34 which engages the ball 26 of the rotor 16. The other stator member 18 located at the outlet 36 includes outlet stator blades 38 and a cup 40 which engages the ball 28 of the rotor 16. A lubricant (either manufacturing fluid, purge fluid, or some constitutive component of blood) fills the gaps created between the ball and cup members 26, 28, 40 and 34. In operation, electrical power is supplied to the motor stator 42 through cable 44 and the motor stator 42 along with the motor rotor 46 imparts rotational movement to the rotor 16 such that blood is pumped through the blood flow path 14 by the motion of the rotor blades 24.

The disadvantage of this type of pump is that the mechanical frictional contact and/or viscous dissipation between the contact-type bearing members creates heat at the bearing interface which may result in coagulation and destruction of blood flowing through the housing blood flow path. Furthermore, the coagulated blood can accumulate in the bearing gap causing seizure.

Nowhere in the cited related art is there disclosed or suggested a rotary pump having a rotor which is rotatably connected to a stator and which provides for the dissipation of heat created from this frictional contact thus, minimizing thermally induced destruction and coagulation of blood. Therefore, there is a definite need for a rotary blood pump which incorporates a semiconductor-based electronic component that dissipates heat created by the frictional contact between the stator and the rotor thus, minimizing damage to the blood flowing through the pump.

SUMMARY OF THE INVENTION

Accordingly, the present invention provides a rotary blood pump having a housing defining a blood flow path, a stator attached to the housing, a rotor rotatably connected to the stator and a semiconductor-based electronic component which transfers heat and wherein the geometric configuration of the blood pump minimizes stagnation of the blood flow. The electronic component draws the heat created by the frictional contact between the stator and rotor away from the blood. Preferably, the electronic component is a semiconductor-based electronic component consisting of one of bismuth-telluride, lead telluride, silicon-germanium and bismuth-antimony. However, other thermoelectric devices which utilize the Peltier effect can be used to dissipate the heat.

The present invention further provides a blood pump which substantially comprises a centrifugal pump having a housing with an integral base plate, a rotor with rotor blades and a stator wherein the geometric configuration of the stator, the rotor hub, the rotor blades and the housing base plate are shaped and proportioned such that blood does not stagnate within the pump. The stator, the rotor, and the housing have mating surfaces which define a profile which promotes and enhances streamlined flow and minimizes blood deposition.

The present invention further provides for a housing having an inlet with a tapered opening in order to increase the velocity of blood flowing therethrough which improves the fluid dynamic washing of the bearing surface.

Other details, objects and advantages of the present preferred invention will become more apparent with the following description of the present preferred invention.

BRIEF DESCRIPTION OF THE DRAWINGS

FIGS. 2c and 2d are exploded views of the cross-section of alternative embodiments of a stator that can be used in the rotary pump of FIG. 2a.

DETAILED DESCRIPTION OF THE PRESENT PREFERRED INVENTION

Although this invention is suitable for other uses it will be described as being used as a blood pump to pump fluid through a patient. Such description is for purposes of explanation and is not intended to limit the scope of this invention.

Figure 1:
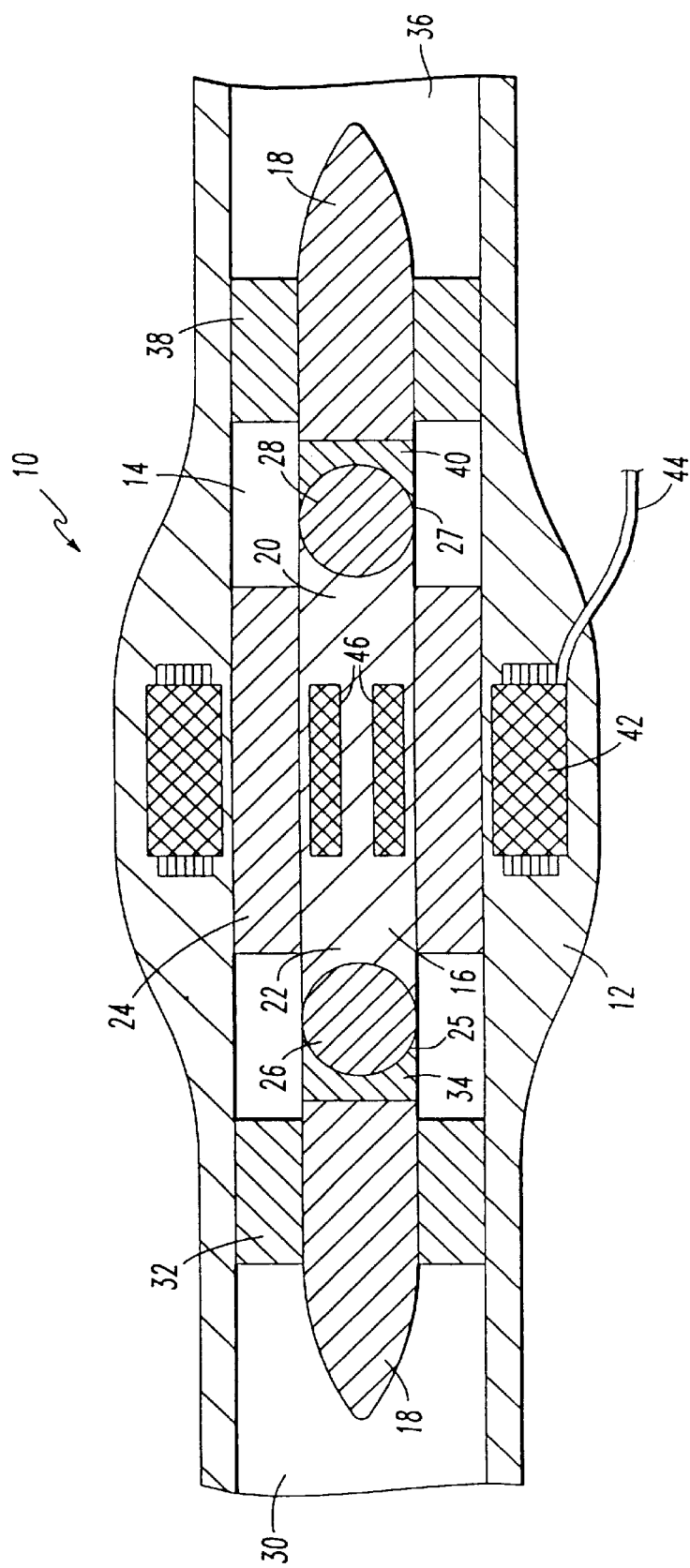
FIG. 1 is a cross-sectional view of a conventional rotary pump.
Figure 2A:
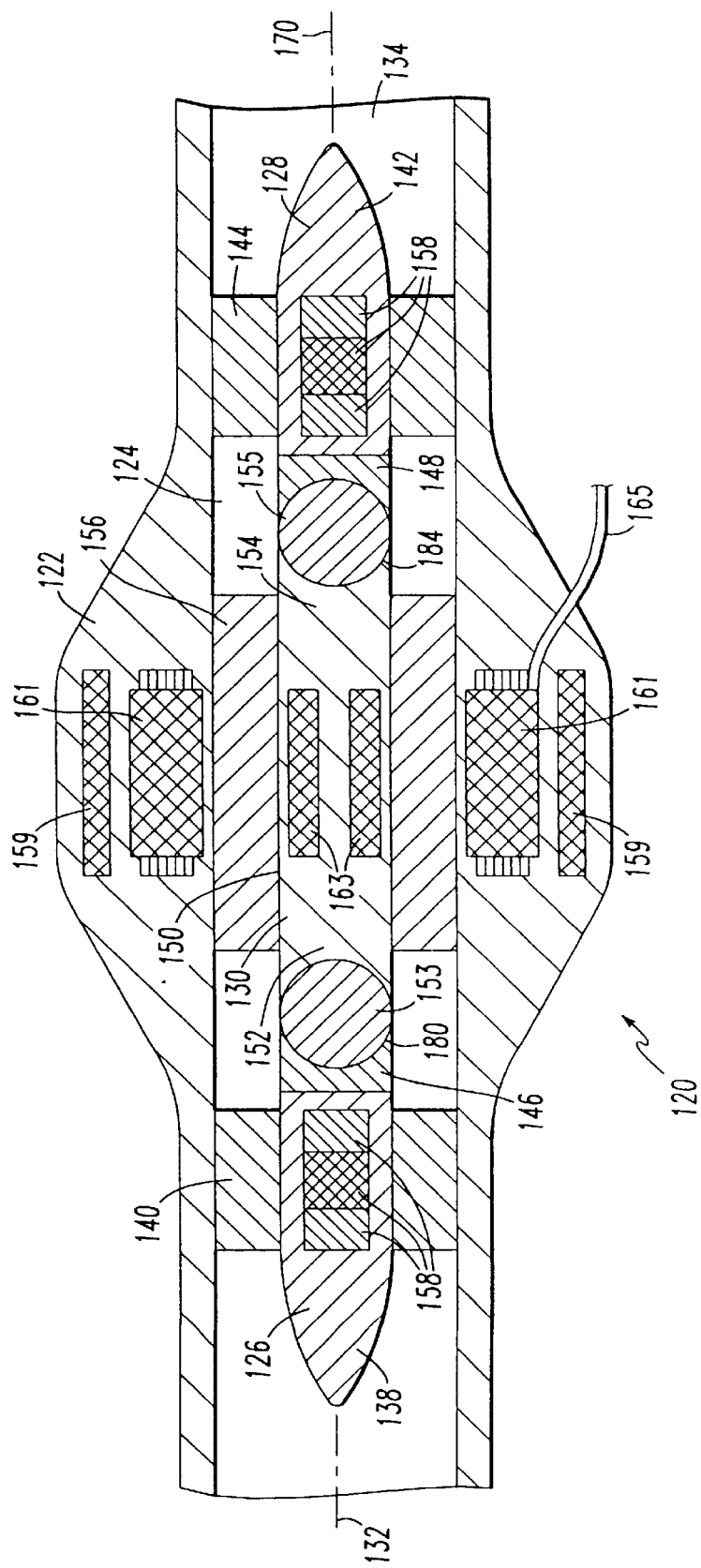
FIG. 2a is a cross-sectional view of one embodiment of a rotary pump which incorporates the present invention.

FIG. 2a illustrates a rotary blood pump 120 substantially comprising a housing 122 which defines a blood flow path 124, two stator members 126, 128 and a rotor 130. The housing 122 has an inlet 132 and an outlet 134. Stator member 126 is attached to the housing 122 at the inlet 132 and stator member 128 is attached to the housing 122 at the outlet 134. Stator member 126 has a shaft 138 and stator blades 140 extending radially from the stator shaft 138. Likewise, stator member 128 has a shaft 142 with radially extending stator blades 144. The shaft 138 has a cup 146 and the shaft 142 has a cup 148. Stationary motor field coils 161 are positioned within the housing 122.

Figure 2B:
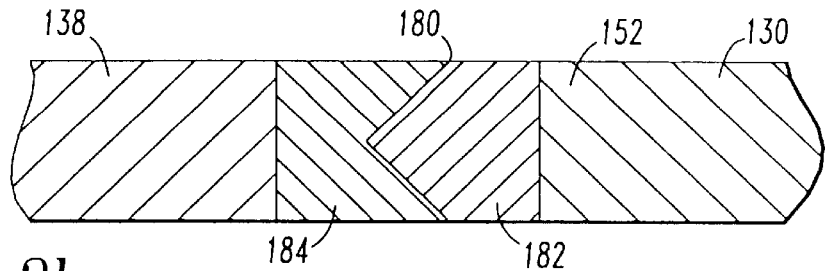
FIG. 2b is a cross-sectional view of a cone-and-cone contact bearing that can be used in the present invention.

The rotor 130 has a substantially cylindrical hub 150 with a nose 152 at one end portion and a tail 154 at the other end portion. A contact-type bearing 180 is positioned at the rotor nose 152 and another contact-type bearing 184 is positioned at the rotor tail 154. The contact-type bearing may be (a) roller-type, (b) journal-type, (c) pivot-type, or (d) any other two member assembly composed of a male member and a necessary member having substantially complementary mating surfaces with identical axi-symmetric profiles, such as a cone-and-cone bearing surface. For the purposes of this discussion, a pivot-type ball-and-cup bearing is assumed, although any of the various contact-type bearings could be equally applicable. FIG. 2b illustrates an example of a cone-and-cone type bearing 180. A substantially conically-shaped bearing 182 is affixed to the rotor 130 and a mating substantially conically-shaped member 184 is attached to the stator shaft 138. Referring back to FIG. 2a, the nose 152 has a ball 153 affixed at the end and the tail 154 has a ball 155 affixed at the end. The rotor balls 153 and 155 contact and are rotatably connected to the stator members cups 146 and 148, respectively. The rotor 130 also has blades 156 extending from the rotor hub 150 and an internal motor rotor 163 made of magnetic material.

Strategically positioned within the stator shafts 138 and 142 are semiconductor-based thermoelectric modules 158 sometimes called thermoelectric coolers or Peltier junctions. The thermoelectric modules 158 are positioned in series to form a heat pump. Additional semiconductor-based electronic components 159 are positioned within the housing 122 adjacent to the stator motor 161. The semiconductor-based electronic components 158 and 159 can be made of many different materials but are preferably made from one of bismuth-telluride, lead telluride, silicon-germanium and bismuth-antimony. By applying a DC power source (not shown) to the semiconductor-based electronic components heat will be moved through the component from one side to the other. One face of the component will be cooled while the opposite face is simultaneously heated. The semiconductor is doped and the application of the DC power to the component causes electrons to move through the semiconductor material. These semiconductor-based electronic components can be obtained from International Thermoelectric, Inc. located in Chelmsford, Mass. In addition, feedback control could be incorporated to maintain a desired temperature. This would involve the addition of a thermal sensor such as a thermocouple or thermistor and a control circuit. However, this additional complexity is not believed to be necessary.

In operation, the blood enters the inlet 132 and is pumped through the housing blood flow path 124 by the rotational movement of the rotor blades 156. The rotor 130 is rotated when power is supplied to the motor stator 161 through cable 165 and is electronically coupled with the rotor motor 163. As stated above, the rotor 130 contacts and is rotatably connected to the stator members 126 and 128 via the balls 153 and 155 and cups 146 and 148 of the rotor 130 and the stator members 126 and 128, respectively. As a result of the frictional contact and/or viscous dissipation of the gap lubricant between the rotor 130 and the stator members 126 and 128, heat is generated at the interface of the balls 153 and 155 and cups 146 and 148. The semiconductor-based electronic components 158 draw the heat from the rotor nose 152 and the rotor tail 154, through the stator shafts 138 and 142, which then conducts into the stator blades 140 and 144 and then into the housing 122. All the while blood is washing each surface of the rotor shaft, the stator blades 140 and 144 and the stator shafts 142 and 138 convecting away the heat. This configuration substantially prevents the blood from being heated and coagulating around the rotor 130 and within the bearing gap resulting in the pump becoming inoperable. The semiconductor-based electronic components 159 similarly dissipate the heat generated by the motor stator 161. The semiconductor-based electronic components 159 draw the heat created by the field coils of the motor stator 161 away from the blood flow path 124 and in a direction substantially perpendicular to and pointing away from the central axis 170 of the housing 122.

Figure 2C:
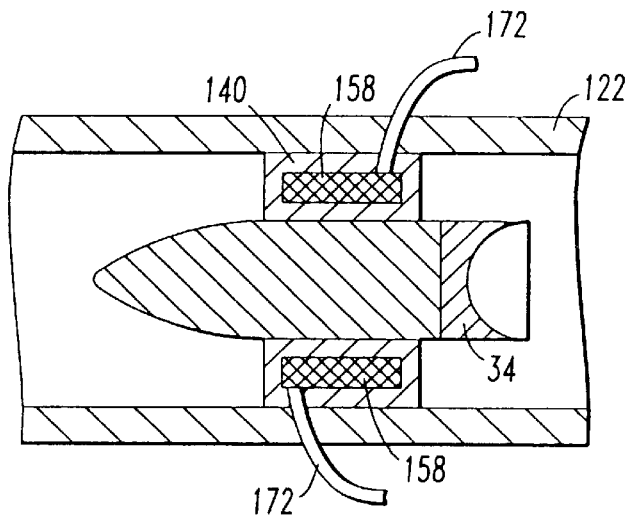
Figure 2D:
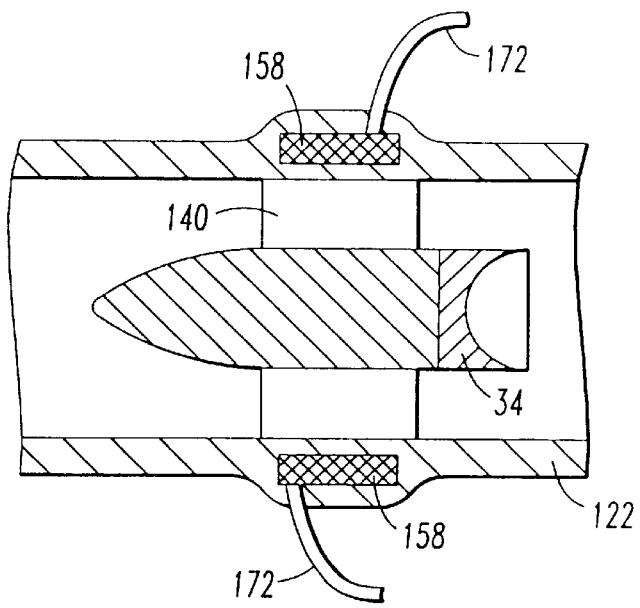

FIG. 2c illustrates an alternative embodiment of the stator blade 140 of the blood pump described in FIG. 2a having semiconductor-based electronic components 158 positioned within the stator blade 140. By repositioning the semiconductor-based electronic components 158 from the stator shafts 138 and 142 into the stator blades 140 and 144, the semiconductor-based electronic components 158 enhance the heat transfer from the bearing to the main blood flow which rapidly advex through the housing flow path 124. Electrical wires 172 are electrically connected to the semiconductor-based electronic components 158 such that a DC power source can be provided to the semiconductor-based electronic components 158. The semiconductor-based electronic components can be positioned in a variety of places within the blood pump depending on where heat is being generated. Also, the semiconductor-based electronic components can be used in various numbers depending on the amount of heat being generated. It is believed that even a small amount of heat removal will improve the biocompatibility of the bearing. However, for optimal effect, sufficient heat must be transported away from the heat-generating elements (bearings, seals, motor windings) so that temperatures of the blood-contacting surface are maintained below 42 degrees Centigrade. For example, FIG. 2d illustrates another embodiment of the stator blade 140 of the blood pump described in FIG. 2a having the semiconductor-based electronic components 158 embedded inside the housing 122, as shown in the top of FIG. 2d, or, alternatively, affixed to the outside of the housing 122, as shown in the bottom of FIG. 2d. If affixed to the outside of the housing 122, it can be positioned within a separate cooling jacket (not shown).

Figure 3:
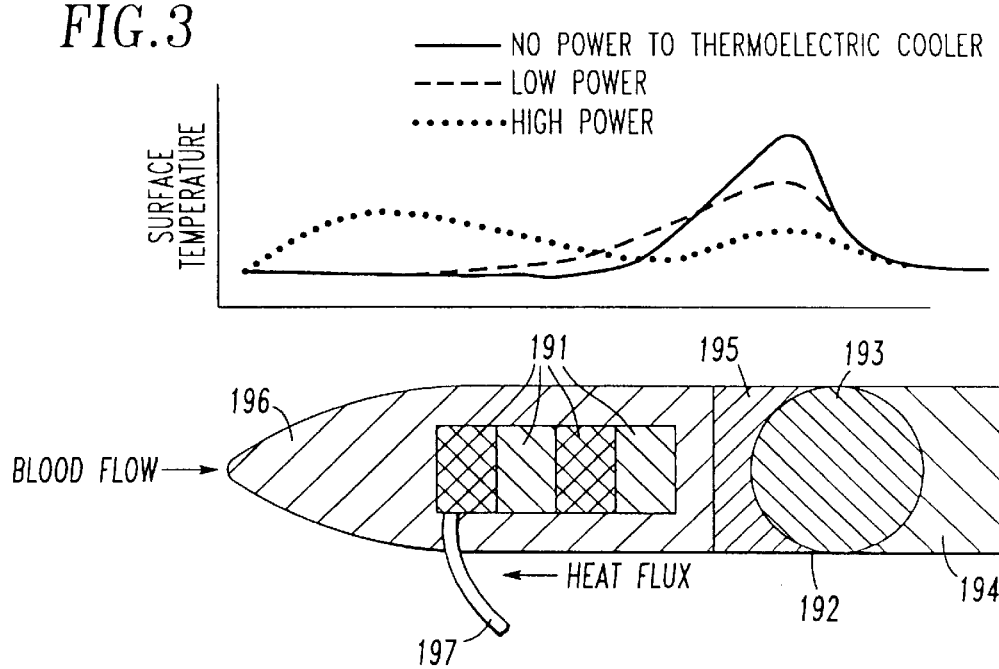
FIG. 3 illustrates the principle of operation by which the semiconductor-based electronic component transfers heat away from the bearing.
Figure 4:
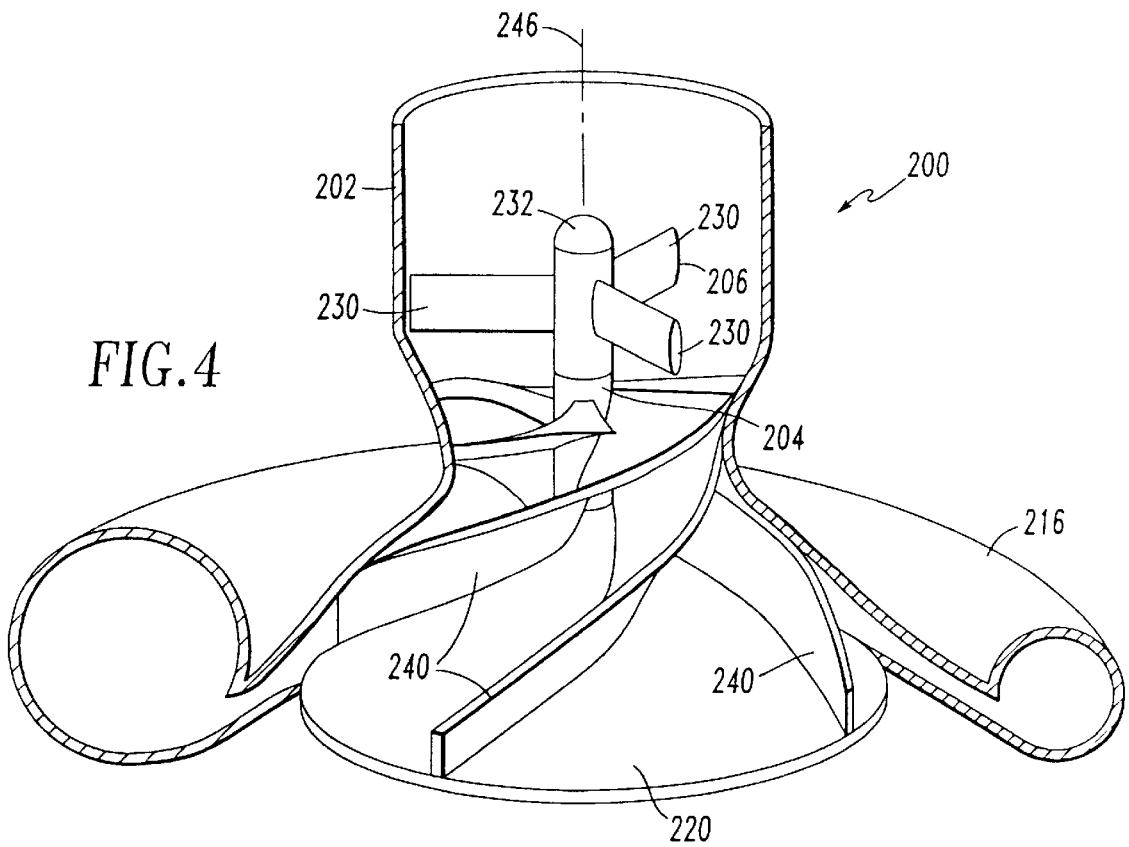
FIG. 4 is a perspective view of another embodiment of the present invention in which the housing is cut-away in order to more clearly illustrate the rotor, the stator and the housing base plate.
Figure 5:
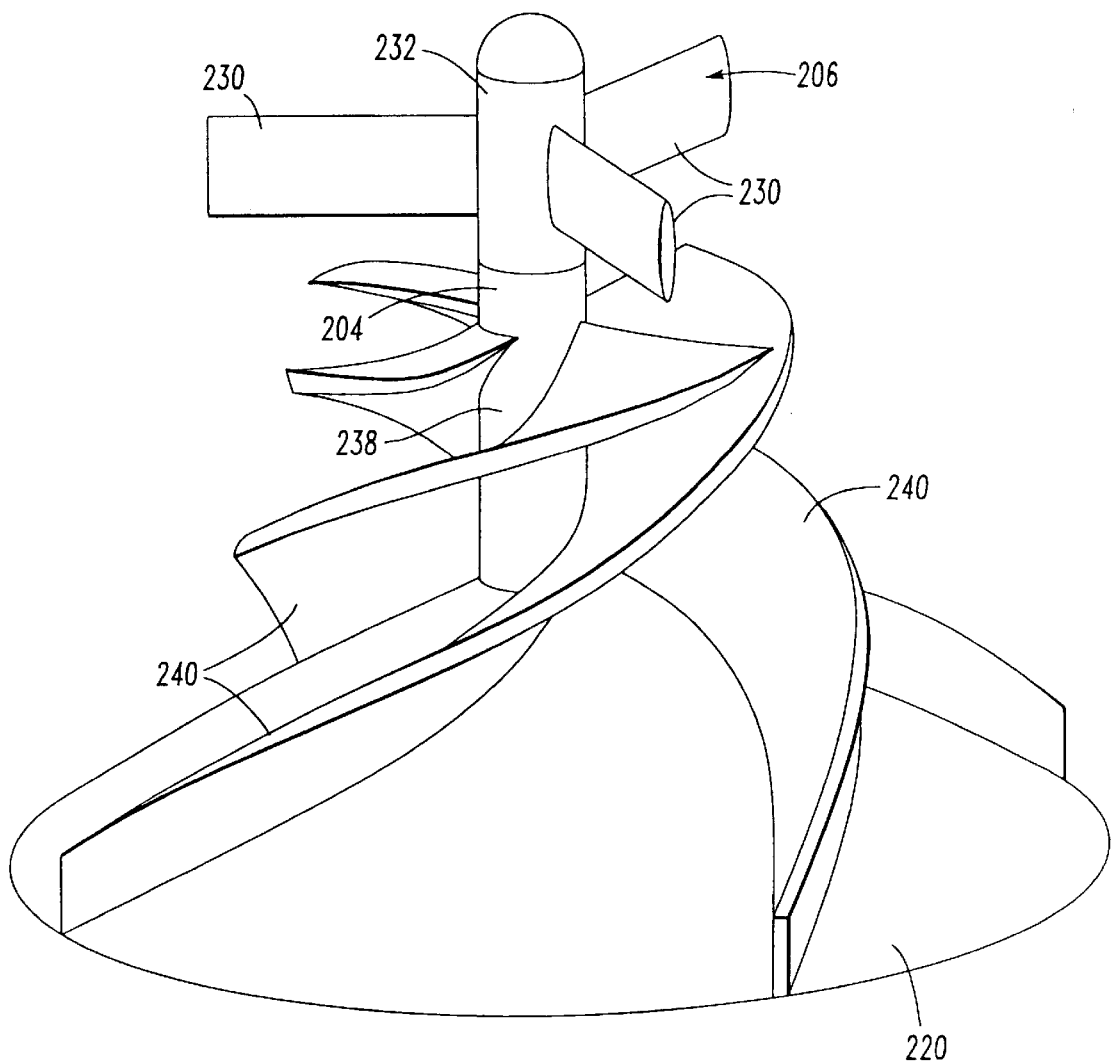
FIG. 5 is a perspective view of the rotor, stator and housing base plate of the centrifugal pump shown in FIG. 4.

FIG. 3 illustrates the principle of operation by which the semiconductor-based thermoelectric coolers 191 transfer heat away from a contact type-bearing 192 made up of a ball 193 affixed to a rotor 194 and a cup 195 affixed to a stator shaft 196. As shown in FIG. 3, a plurality of thermoelectric coolers 191 may be arranged in series such that a heat pump is formed to transfer heat along the length of a stator shaft 196. The amount of DC power supplied to the thermoelectric coolers via electrical wires 197 determines the effectiveness of the thermoelectric coolers to transfer the frictional heat generated by the contact-type bearing 192 away from the bearing interface. The generated heat is manifested as locally elevated surface temperatures. The heat is ultimately convected away by blood flow adjacent to the rotor shaft, the stator shaft and bearing surfaces and/or conducted along the stator blades (not shown) and convected away by the main blood flow passing over the stator blades and rapidly advexing through the housing flow path 124.

FIGS. 4–6b illustrate another preferred embodiment of the present invention which takes the form of a centrifugal pump 200. The centrifugal pump 200 substantially comprises a housing 202 with an integral volute 216, an open-style rotor 204 and a stator 206 wherein the housing 202 defines a flow path 210. The volute 216 is designed so as to optimize blood flow and minimize blood stagnation and blood trauma. The housing 202 further has a cylindrical blood inlet portion 212, a truncated cone portion 214 with the volute 216 positioned around the periphery 218 of the cone 214 and a substantially conically shaped base plate 220. The volute 216 has an outlet (not shown). Although not described, it should be understood that the base plate can take other forms such as concave. The cylindrical inlet portion 212 defines an opening 222 which is tapered at 224 and subsequently increases in diameter as blood proceeds through the blood flow path 210. Motor field coils 228 are positioned in the motor housing 221 which may be an integral or separate unit to the housing 202. Semiconductor-based electronic components 229 are positioned within the stator shaft 232 and another semiconductor-based electronic component 231 is positioned within the base plate 220 of the housing 202.

The stator 206 has thermally conductive stator blades 230 which radially extend from a stator shaft 232 and are fixed to the inlet portion 212 of the housing 202. The stator 206 has a cup 236 at one end of the stator shaft 232.

The rotor 204 has a rotor shaft 238 and helical open-style rotor blades 240 which extend radially from the rotor shaft 238. Magnets 242 are placed within the rotor blades 240 adjacent to the field coils 228 such that the rotating magnetic field produced rotates the rotor 204 about its axis 246. A contact-type bearing 250 is positioned at the rotor nose 252 and another contact-type bearing 254 is positioned at the rotor tail 256. The contact-type bearings may be (a) roller-type, (b) journal-type, (c) pivot-type, or (d) any other two member assembly composed of a male member and a necessary member having substantially complementary mating surfaces with identical axi-symmetric profile such as a cone-and-cone bearing surface. For the purposes of this discussion, a pivot-type ball-and-cup bearing will be assumed, although any of the various contact-type bearings could be equally applicable. The rotor 204 has a ball 258 affixed at both ends of the rotor shaft 238. The balls 258 are rotatably connected to the stator cup 236 and the housing cup 260 such that the rotor 204 is rotatably connected with the stator 206 and the housing 202.

The rotor shaft 238, the stator shaft 232 and the housing base plate 220 are designed to follow a common profile 259, although the region comprising the rotor shaft 238 is rotating, while the regions comprising the housing baseplate 220 and stator shaft 232 are stationary. This profile, shown in FIG. 6b in bold line, is designed to promote and enhance the convective transport ("washing" action) of heat and other platelet agonist away from the rotor shaft 238, the stator shaft 232 and housing base plate 220 surfaces, thus assuring streamlined flow avoiding dead-space region and blood-element deposition.

In operation, blood enters through inlet portion 212 and is pumped through the centrifugal pump housing 202 by rotor blades 240 and exits through the volute outlet. As blood passes through the inlet portion 212, it contacts the stator blades 230. The inlet portion 212 then decreases in diameter resulting in increased blood velocity and hence improved washing of the bearing 250. Once past the tapered portion at 224, the blood enters the portion of the housing 202 defined by the truncated cone 214 where it contacts the rotating rotor blades 240 which are sweeping across the housing base plate 220. As the rotor blades 240 rotate they continuously move the blood over and above the housing base plate 220 and the rotor blades 240 such that blood stagnation and coagulation will be minimized at the rotor blades 240, the base plate 220 and the bearing 250. As the rotor 204 rotates about its axis 246, heat is generated by the frictional contact between the rotor balls 258 and the cups 260 and 236. This heat is drawn from the ball and cup interface through the stator 206 and the base plate 220 away from the blood flow path 210 by the semiconductor-based electronic components 229 and 231, respectively. Although not shown, the field coils 228 are electrically connected to a power source such that when power is supplied to the field coils 228 the magnetic coupling between the field coils 228 and the magnetic material 242 within the rotor blades 240 rotate the rotor 204.

Figure 6A:
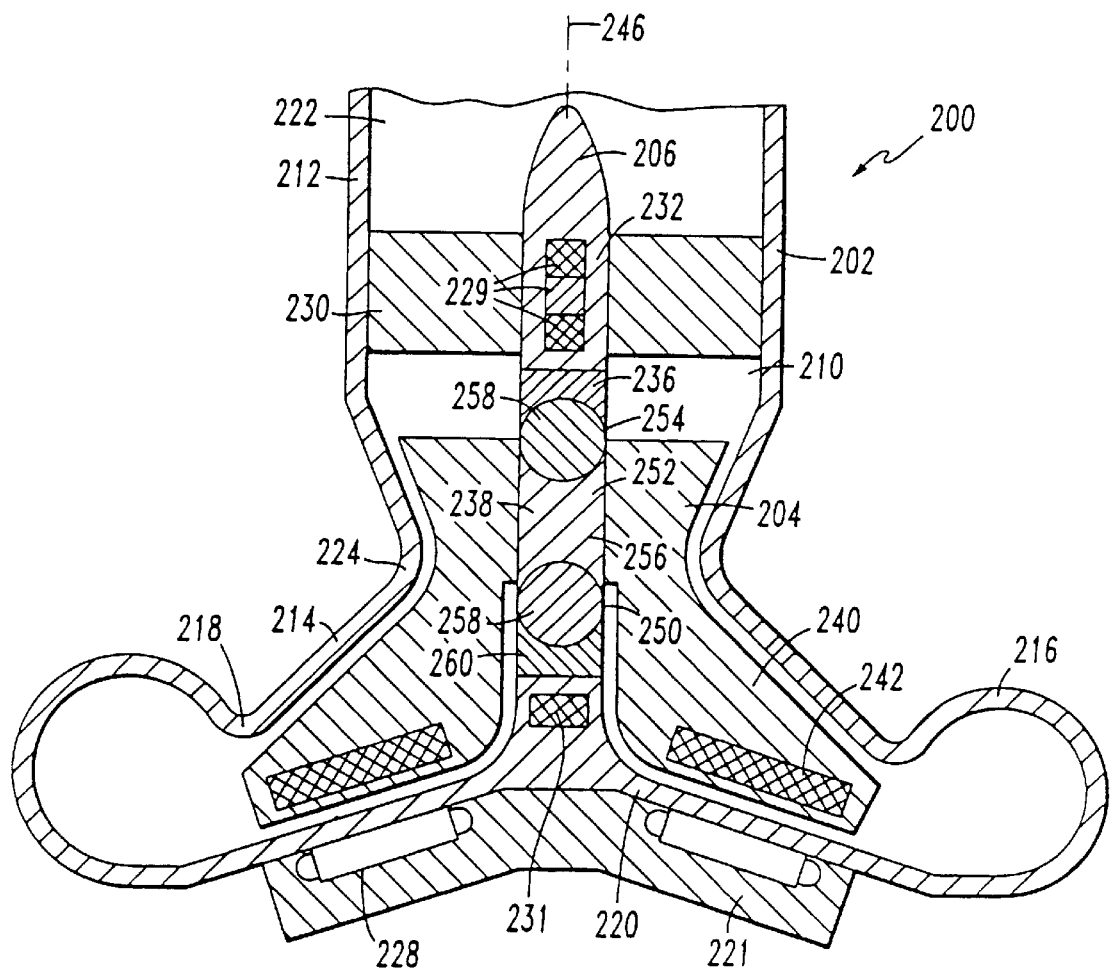
FIG. 6a is a cross-sectional view of the centrifugal pump shown in FIG. 4.
Figure 6B:
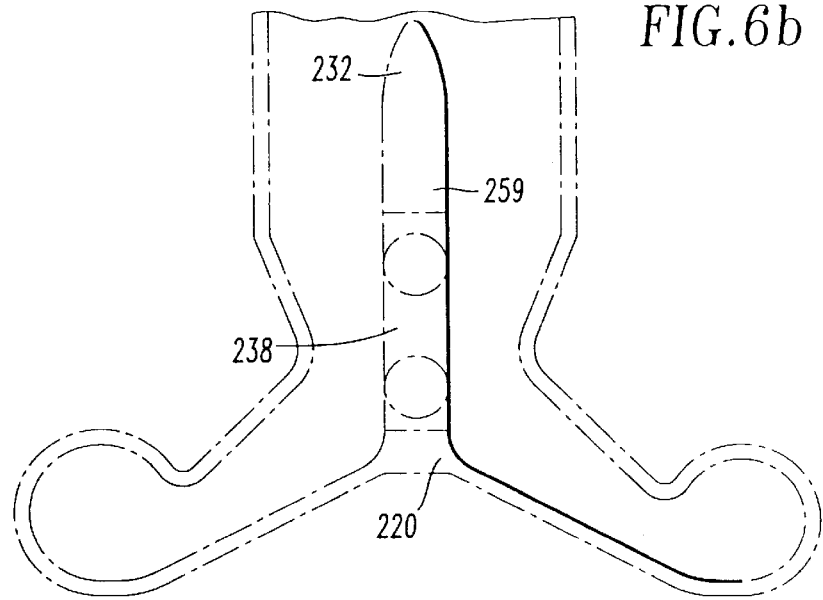
FIG. 6b is a cross-sectional view of the pump shown in FIG. 6a with the profile illustrated in solid line and the other features shown in hidden line.
Figure 6C:
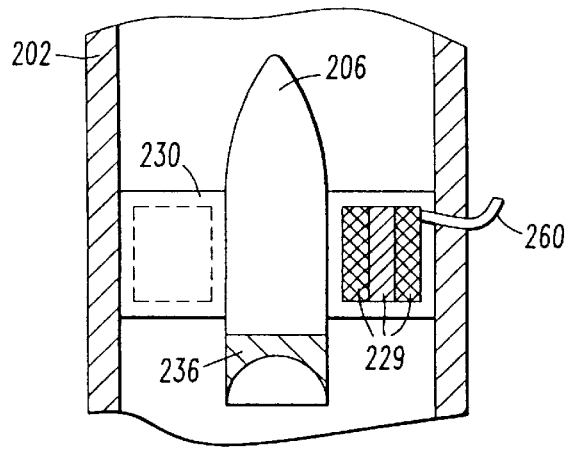
FIGS. 6c and 6d are exploded views of the cross-sections of alternative positions of semiconductor-based electronic components that can be used in the centrifugal pump shown in FIG. 4.
Figure 6D:
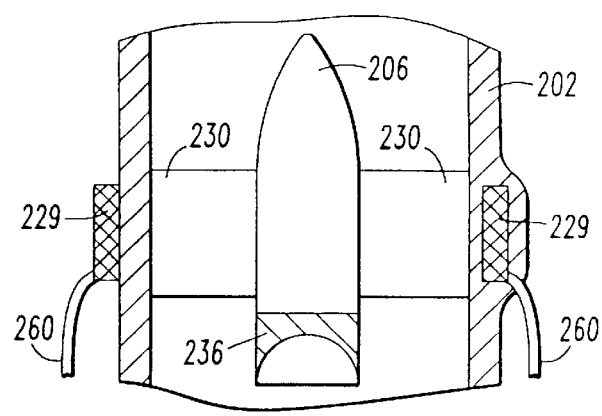

FIG. 6c shows an alternative embodiment of the stator blades 230 of the blood pump 200 shown in FIG. 6a wherein a series of semiconductor-based electronic components 229 are positioned within the stator blades 230 and have wires 260 to supply power to the semiconductor-based electronic components 229. As stated above, the semiconductor-based electronic components 229 and 231 can be positioned in a variety of positions depending on where heat is generated and the amount of the heated needed to be dissipated. For example, FIG. 6d illustrates an alternative positioning of the semiconductor-based electronic components 229 having the semiconductor-based electronic components 229 embedded inside the housing 202, as shown on the right side of FIG. 6d, or alternatively, affixed to the outside of the housing 202, as shown on the left side of FIG. 6d. Also, the semiconductor-based electronic components can be positioned external to the housing within a separate cooling jacket surrounding the inlet.

The connection of the pump to the body can be accomplished in any number of ways disclosed in the prior art and readily familiar to anyone utilizing such pumps for cardiac surgery or implanting such pumps as permanent ventricular assist devices.

Although the present invention is described above as having a magnetically coupled motor, other devices for rotating the rotor can be used, such as a direct drive shaft motor.

While the present invention has been described herein, it is distinctly understood that the invention is not limited thereto but may be otherwise variously embodied in the scope of the following claims and any equivalent thereof.

We claim:

1. A blood pump for pumping blood that prevents coagulation of blood flowing through the pump by maintaining the blood flowing through the pump below a threshold temperature at which the blood coagulates, comprising:

(a) a housing that has an inlet and an outlet;

(b) a stator, disposed within and attached to the housing by a plurality of stator blades extending from the stator to the housing, a blood flow path being defined between the stator and the housing and between each of the stator blades, (c) a rotor, disposed within the housing between the inlet and the outlet, and having an end that is coupled to the stator by a mechanical bearing that generates heat during operation of the pump, the mechanical bearing comprising a first bearing gap, disposed between the mechanical bearing and the rotor, so that blood can flow through the first bearing gap and lubricate the bearing;

(d) a mechanism that imparts rotational movement to the rotor; and (e) at least one electronic component, disposed within the stator proximal to the mechanical bearing, and wherein during operation of the pump the electronic component draws heat from (i) the rotor; (ii) the mechanical bearing, and (iii) the blood flowing proximal to the mechanical bearing and through the first bearing gap and the blood flowing proximal to the rotor, and transfers heat, via conductive heat transfer, to the stator and the housing, the stator and the housing transferring heat via advective convection to the blood flowing along the flow path and thereby maintaining the temperature of the blood below the threshold temperature and preventing coagulation of the blood.

2. The blood pump of claim 1 wherein the at least one electronic component is a thermoelectric cooler.

3. The blood pump of claim 2 wherein the thermoelectric cooler is a semiconductor-based electronic component.

4. The blood pump of claim 3 wherein the semiconductor-based electronic component is selected from the group consisting of one of bismuth-telluride, lead telluride, silicon-germanium and bismuth-antimony.

5. The blood pump of claim 3 wherein the semiconductor based electronic component is bismuth-telluride.

6. The blood pump of claim 1, wherein the mechanical bearing further comprises a second bearing gap being disposed between the mechanical bearing and the stator, so that the lubricating blood can lubricate the bearing.

7. The blood pump of claim 1 wherein the rotational mechanism is an electric motor, disposed within the housing that generates heat, and the blood pump further comprises a second electronic component, disposed within the housing, which draws heat created by the electric motor away from an inner surface of the housing along which blood flows and to an exterior surface of the housing to prevent the blood flowing along the blood flow path proximate to the inner surface from exceeding the threshold temperature.

8. A centrifugal rotary blood pump for pumping blood through a patient that maintains the blood flowing through the pump below a threshold temperature at which the blood coagulates, comprising:

(a) a housing having an inlet, an outlet and a base plate;

(b) a stator attached to the housing at the inlet by a plurality of stator blades;

(c) a rotor rotatably connected to both the stator and the housing, the rotor having rotor blades that are shaped and proportioned such that when the rotor blades rotate, the rotor blades sweep across the base plate and blood is substantially prevented from collecting between the rotor blades and the housing base plate, a blood flow path being defined over the stator blades and between the rotor and the housing;

(d) a first blood lubricated mechanical bearing that couples the rotor to the stator and said first bearing having a passage through which blood flows to provide lubrication;

(e) a second blood lubricated mechanical bearing that couples the rotor to the housing and said second bearing having a passage through which blood flows to provide lubrication;

(f) a motor, disposed within the housing, for imparting rotational movement to the rotor;

(g) a first thermoelectric cooler positioned within the stator proximate to the passage in the first blood lubricated mechanical bearing, the first thermoelectric cooler during operation of the pump transferring heat, generated by the first mechanical bearing, from the rotor, the blood flowing proximate to the rotor, the lubricating blood of the first mechanical bearing and the first mechanical bearing, through the stator and to the stator blades, so that the blood flowing along the blood flow path over the stator blades can absorb the heat from the stator blades, and thereby cool the rotor and the first mechanical bearing to maintain the blood flowing proximate to the rotor and the first mechanical bearing below the threshold temperature;

(h) a second thermoelectric cooler positioned within the housing proximate to the passage in the second blood lubricated mechanical bearing, the second thermoelectric cooler during operation of the pump transferring heat, generated by the second mechanical bearing, from the rotor, the blood flowing proximate to the rotor, the lubricating blood of the second mechanical bearing and the second mechanical bearing, to the housing, so that the blood flowing past the housing can absorb the heat from the housing, and thereby cool the rotor and the second mechanical bearing to maintain the blood flowing proximate to the rotor and the second mechanical bearing below the threshold temperature.

9. The centrifugal blood pump of claim 8 wherein the housing base plate, the rotor and the stator are shaped and proportioned to form a common smooth profile which minimizes blood stagnation and coagulation between the rotor, the stator and the housing and promotes streamlined flow through the housing.

10. The centrifugal blood pump of claim 9 wherein the housing has a three dimensional truncated substantially conical surface.

11. The centrifugal blood pump of claim 10 further comprising a volute which extends around the periphery of the truncated cone.

12. The centrifugal blood pump of claim 8 wherein the first blood lubricated mechanical bearing comprises a ball and cup bearing.

13. The centrifugal blood pump of claim 8 wherein the inlet defines an opening which is tapered inwardly such that the cross-section of the opening decreases and subsequently increases.

14. The centrifugal rotary blood pump of claim 8 wherein the first mechanical bearing and the second mechanical bearing comprise surfaces that are substantially complimentary mating surfaces with identical axi-symmetric profiles such that they form rotatable connections between the respective bearing and the rotor.

15. The centrifugal rotary blood pump of claim 8 wherein the first mechanical bearing comprises a cone-and-cone contact bearing.

16. A rotary blood pump for pumping blood through a patient and maintaining the blood flowing through the pump below a temperature at which the blood coagulates, comprising:

(a) a housing having an inlet and an outlet;

(b) a first stator member, disposed at the inlet, having a first hub and a first set of stator blades extending from the first hub to the housing;

(c) a second stator member, disposed at the outlet, having a second hub and a second set of stator blades extending from the second hub to the housing;

(d) a rotor, disposed between the inlet and the outlet, and rotatably connected to the first stator member by a first blood lubricating mechanical bearing and rotatably connected to the second stator member by a second blood lubricating bearing, each of the first and the second bearings having gaps through which blood flows to lubricate the bearings;

(e) a motor which imparts rotational movement to the rotor; and (f) a first thermoelectric device, disposed in the first stator member adjacent to the first mechanical bearing, so that the first thermoelectric device draws heat generated by the first mechanical bearing away from the rotor, the first mechanical bearing, the lubricating blood and the blood flowing proximate to a periphery of the rotor and transfers heat to the first set of stator blades via conductive heat flow, so that the first set of stator blades transfers heat via advective convection to blood flowing around the first set of stator blades to thereby prevent the temperature of the lubricating blood and the blood flowing proximate to the periphery of the rotor from reaching the threshold temperature; and (g) a second thermoelectric device, disposed in the second stator member adjacent to the second mechanical bearing, so that the second thermoelectric device draws heat generated by the second mechanical bearing away from the rotor, the second mechanical bearing, the lubricating blood and the blood flowing proximate to the periphery of the rotor and transfers heat to the second set of stator blades via conductive heat flow, so that the second set of stator blades transfers heat via advective convection to blood flowing around the first set of stator blades to thereby prevent the temperature of the lubricating blood and the blood flowing proximate to the periphery of the rotor from reaching the threshold temperature.

17. The rotary blood pump of claim 16 wherein the first thermoelectric device is at least one semiconductor-based electronic component.

18. The rotary blood pump of claim 16 wherein the first blood lubricating mechanical bearing comprises a cone-and-cone contact bearing.

19. The rotary blood pump of claim 16 wherein the first mechanical bearing and the second mechanical bearing comprise surfaces that are substantially complimentary mating surfaces with identical axi-symmetric profiles such that they form rotatable connections between the respective bearing and the rotor.

20. A method of maintaining blood in a blood pump below a threshold temperature at which the blood tends to coagulate, comprising:

rotating a rotor disposed within a housing of the blood pump to provide an impetus for blood to pass through the housing;

lubricating a mechanical bearing that couples the rotor to a stator, disposed within the housing at an inlet of the housing, by passing blood proximal to the mechanical bearing;

generating heat from operation of the mechanical bearing;

transferring heat from the mechanical bearing, the rotor, the blood passing proximate to the rotor, the mechanical bearing and the lubricating blood to the stator with a first thermoelectric cooler disposed within the stator;

passing heat from the stator to the stator blades extending from the stator to the housing; and distributing heat from the stator blades to the blood flowing through the pump by passing blood over the stator blades.

21. The method of claim 20, further comprising transferring heat generated by a motor in the housing from the housing to an external surface of the housing with a second thermoelectric cooler disposed within the housing and thereby preventing blood passing proximate to an inner surface of the housing from being heated above the threshold temperature.

* * * * *